United States Patent [19]

de Sousa et al.

[11] Patent Number: 4,602,912

[45] Date of Patent: Jul. 29, 1986

[54] MOTHPROOFING AND BEETLEPROOFING COMPOSITION: 5-(PYRIDYLOXY- OR THIOTHENYLCARBAMOYL)BARBITURIC ACID

[75] Inventors: Bernardo de Sousa, Riehen; Urs Burckhardt, Basel; Jean J. Gallay, Magden; Manfred Kühne, Pfeffingen; Ernst Beriger, Allschwil, all of Switzerland; Dieter Reinehr, Kandern, Fed. Rep. of Germany

[73] Assignee: Ciba-Geiby Corporation, Ardsley, N.Y.

[21] Appl. No.: 748,282

[22] Filed: Jun. 24, 1985

[30] Foreign Application Priority Data

Jun. 27, 1984 [CH] Switzerland ............... 3096/84

[51] Int. Cl.[4] .................. A23F 3/34; D06M 3/00; D06P 5/00
[52] U.S. Cl. .................... 8/127.5; 8/128 R; 8/490; 8/499; 8/917; 252/8.6; 252/8.8; 252/8.9; 427/421; 427/428; 514/271; 544/301
[58] Field of Search ............. 8/490, 127.5, 128 R; 252/8.6, 8.8, 8.9

[56] References Cited

U.S. PATENT DOCUMENTS

| | | | |
|---|---|---|---|
| 4,219,593 | 8/1980 | Muntwyler et al. | 428/473 |
| 4,239,762 | 12/1980 | Kramer et al. | 514/270 |
| 4,283,444 | 8/1981 | de Sousa et al. | 514/66 |
| 4,399,280 | 8/1983 | de Sousa et al. | 544/301 |
| 4,503,100 | 3/1985 | de Sousa et al. | 252/8.6 |

FOREIGN PATENT DOCUMENTS

| | | |
|---|---|---|
| 11789 | 6/1980 | European Pat. Off. . |
| 2024625 | 1/1980 | United Kingdom . |

*Primary Examiner*—A. Lionel Clingman
*Attorney, Agent, or Firm*—Edward McC. Roberts; Irving M. Fishman

[57] ABSTRACT

The invention relates to a composition for protecting keratinous material, in particular woollen textiles, from attack by pests that feed on keratin, in particular moth and beetle larvae, which composition contains, as active ingredient combination, a specifically substituted 5-(pyridyloxyphenylcarbamoyl)barbituric acid or a salt thereof and a synthetic pyrethroid, as well as to a process comprising the use of this active ingredient combination for providing said material with a protective finish against attack by pests that feed on keratin.

34 Claims, No Drawings

MOTHPROOFING AND BEETLEPROOFING COMPOSITION: 5-(PYRIDYLOXY- OR THIOTHENYLCARBAMOYL)BARBITURIC ACID

The present invention relates to a composition for protecting keratinous material from attack by pests that feed on keratin, in particular to a composition for protecting wool, furs and feathers from attack and feeding damage caused by moth and beetle larvae, and to a process for protecting said materials from attack by pests that feed on keratin.

It is known that certain synthetic pyrethroids can be used for controlling pests that feed on keratin [q.v. e.g. J. Text. Inst. 1976, No. 3, Vol. 67, 77; Japanese published application No. 58 341; German published application No. 2 923 217; U.S. published application U.S. Pat. No. 4,219,593 and European patent specification No. 11 789]. Said pyrethroids are very effective against moth larvae, whereas their action against the larvae of the fur beetle and carpet beetle is less pronounced. Moreover, it is known from U.S. published application U.S. Pat. No. 4,283,444 that certain 5-phenylcarbamoylbarbituric acids can likewise be used for controlling pests that feed on keratin. Said barbituric acids exhibit a particularly good action against the larvae of the fur beetle and carpet beetle. U.S. published application U.S. Pat. No. 4,283,444 also discloses compositions which contain a combination of the above synthetic pyrethroids and 5-phenylcarbamoylbarbituric acids, with the aid of which combination keratinous material (e.g. wool) can be provided with excellent protection against pests that feed on keratin. European published application No. 105 030 likewise relates to such compositions which contain a combination of synthetic pyrethroids and specific 5-phenylcarbamoylbarbituric acids [e.g. 5-(phenoxyphenylcarbamoyl)barbituric acids].

The compositions of the present invention likewise contain a synthetic pyrethroid and specifically substituted 5-phenylcarbamoylbarbituric acids. Said compositions differ in character from the above-mentioned known compositions in that the phenyl ring in the 5-phenylcarbamoylbarbituric acid component is substituted by a pyridyloxy or pyridylthio radical. The compositions of the invention exhibit excellent protective action on keratinous materials, in particular on wool, against pests that feed on keratin, even when applied at very low concentrations.

The compositions of the invention contain
(A) one or more 5-phenylcarbamoylbarbiturates of the formula

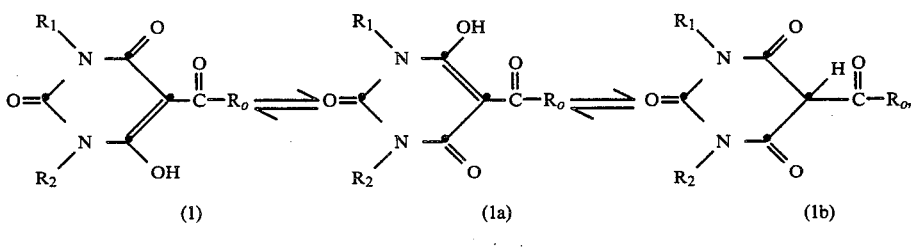

wherein each of $R_1$ and $R_2$ independently is $C_1$–$C_4$alkyl, $C_3$–$C_6$cycloalkyl, $C_2$–$C_4$alkenyl, benzyl, phenyl or phenyl substituted by 1 to 3 substituents selected from the group consisting of halogen, $C_1$–$C_4$alkyl, $C_1$–$C_4$alkoxy and nitro, each of $R_3$ and $R_4$ independently is hydrogen, halogen, $C_1$–$C_4$haloalkyl, $C_1$–$C_4$alkyl, $C_2$–$C_4$alkenyl, $C_3$–$C_6$cycloalkyl or methoxy, each of $R_5$ and $R_6$ independently is hydrogen, halogen, $C_1$–$C_4$alkyl, $C_1$–$C_4$haloalkyl or methoxy and X is oxygen or sulfur, or tautomeric forms or salts thereof, and (B) one or more synthetic pyrethroids.

Compositions of the invention contain for example such compounds of formula (1) wherein X is oxygen and the pyridine ring is attached through the 2-position to the oxygen atom.

The 5-phenylcarbamoylbarbiturates of formula (1) (component (A)) exist in different tautomeric forms (keto/enol tautomerism), for example in accordance with the following scheme:

$$\text{(1)} \rightleftharpoons \text{(1a)} \rightleftharpoons \text{(1b)}$$

in each of which formulae above $R_o$ is the radical

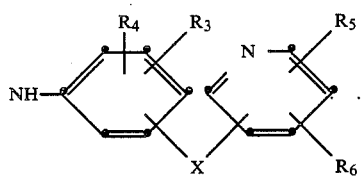

All tautomeric forms and mixtures thereof can be employed in the composition of the invention. Accordingly, the individual formulae also comprise the respective possible tautomeric forms.

The compounds of formula (1) can be used in the composition of the invention in the form of their salts. Such salts are in particular the alkali metal, ammonium or amine salts, preferably the sodium, potassium, ammonium or alkylamine, especially triethylamine, salts.

Of the 5-phenylcarbamoylbarbituric acid compounds of formula (1), it is preferred to use such compounds wherein X is oxygen.

Preferred compounds of formula (1) are of the formula

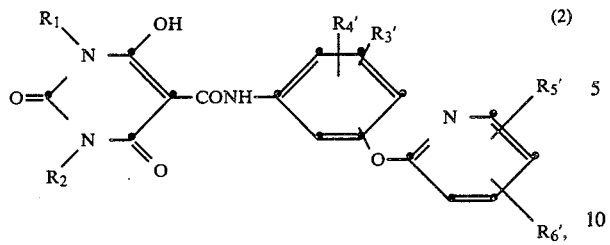

wherein $R_1$ and $R_2$ are as defined for formula (1) and each of $R_3'$, $R_4'$, $R_5'$ and $R_6'$ independently is hydrogen, halogen, $C_1$–$C_4$alkyl, $C_1$–$C_4$haloalkyl or methoxy.

In compounds of formula (1) or (2) the substituent

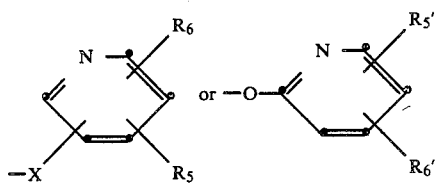

is preferably in ortho- or para-position. $R_1$ and $R_2$ in formula (1) or (2) are preferably $C_1$–$C_4$alkyl, in particular methyl or ethyl.

"Halogen" will be understood as meaning in particular fluorine, chlorine or bromine, preferably chlorine and fluorine.

Preferred $C_1$–$C_4$haloalkyl radicals (substituents $R_3$, $R_4$, $R_5$ and $R_5$ in formula (1)) are those containing 1 or 2 carbon atoms and 1 to 5 identical or different halogen atoms, in particular fluorine or chlorine atoms. Examples of such haloalkyl radicals are: 1,1,2-trifluoro-2-chloroethyl, 1,1,2,2-tetrafluoroethyl, 1,1,2,2-tetrafluoro-2-chloroethyl, chlorodifluoromethyl, dichlorofluoromethyl, dichloromethyl, difluoromethyl, trichloromethyl and, in particular, trifluoromethyl.

In further preferred compounds of formula (1) or (2) $R_1$ is methyl, ethyl, cyclopropyl or allyl, preferably methyl, $R_2$ is ethyl or methyl, preferably methyl, each of $R_3$ and $R_4$ or each of $R_3'$ and $R_4'$ independently is hydrogen, halogen, in particular chlorine, or $C_1$–$C_4$alkyl and each of $R_5$ and $R_6$ or each of $R_5'$ and $R_6'$ independently is hydrogen, halogen, in particular chlorine, or $C_1$–$C_4$haloalkyl, in particular trifluoromethyl, and the substituent

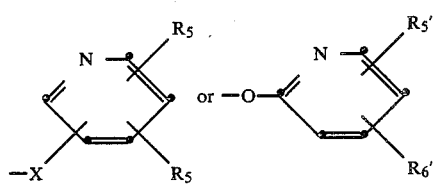

is in ortho- or para-position.

Compositions of the invention which exhibit particularly good activity are those containing as component (A) a compound of formula (2), wherein $R_1$ is allyl or methyl, preferably methyl, $R_2$ is methyl, each of $R_3'$ and $R_4'$ independently is hydrogen, chlorine or methyl and each of $R_5'$ and $R_6'$ independently is hydrogen, chlorine or trifluoromethyl.

Particularly interesting compositions are those wherein the radical

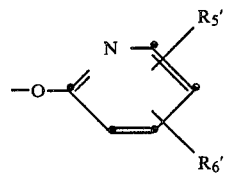

in component (A) of formula (2) is in para-position and $R_5'$ is trifluoromethyl and $R_6'$ is hydrogen.

Particularly suitable as component (A) are the compounds 1,3-dimethyl-5-[4-(3,5-dichloropyrid-2-yloxy)-phenylcarbamoyl]barbituric acid and, in particular, 1,3-dimethyl-5-[4-(5-trifluoromethylpyrid-2-yloxy)-phenylcarbamoyl]barbituric acid.

The second component (component B) of the active ingredient combination of the invention is a synthetic pyrethroid. Preferred pyrethroids in in compositions of the invention belong to the class of cyclopropanecarboxylates or α-alkylphenylacetates, in particular isopropylphenylacetates, i.e. they contain the structural elements

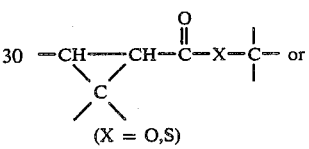

(X = O,S)

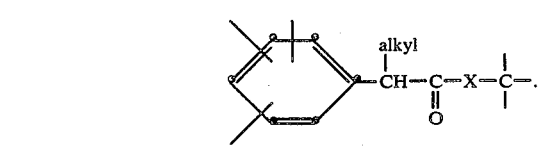

Compounds used as pyrethroid component are for example compounds of the general formula

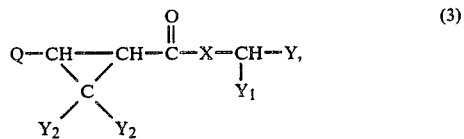

wherein
Q is $Br_2C{=}Br{-}$,

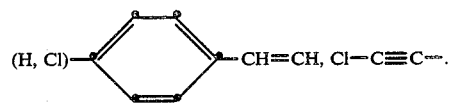

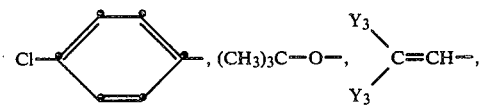

wherein $Y_3$ is Cl, Br, $CF_3$, F or $C_1$–$C_4$alkyl, $CH_2{=}CH{-}CH_2{-}O{-}$ or

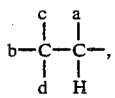

wherein each of a, b, c and d independently is Cl, Br or F, and c and d may also be methyl, X is oxygen or sulfur, $Y_1$ is hydrogen, CN, $CH_3$, $C_2H_5$, i—$C_3H_7$,

—C≡CH, —C≡C—$CH_3$, —C≡C—$C_6H_5$, —CH=CH—$CH_3$, —$CH_2$—CH=$CH_2$, —CH=$CH_2$ or —$CH_2$—CH=CHCl, $Y_2$ is methyl or both substituents $Y_2$ together complete a cyclopropane, cyclobutane or cyclopentane ring, and Y is

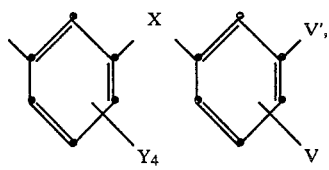

wherein $Y_4$ is hydrogen or fluorine and V is hydrogen, Cl, Br, F, $CH_3$ or $NO_2$ and V' is hydrogen, with the proviso that, when V is hydrogen, V' may also be $CF_3$, and X is as defined above; or Y is

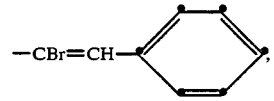

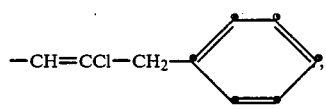

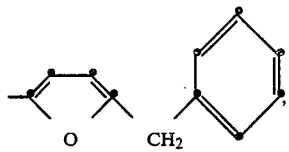

wherein $V_1$ is —$CH_2$—CH=$CH_2$, —$CH_2$—C≡CH,

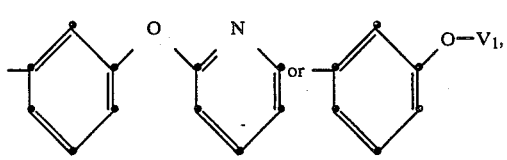

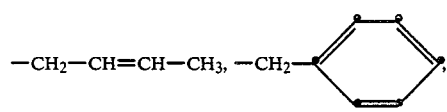

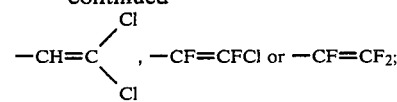

or of the general formula

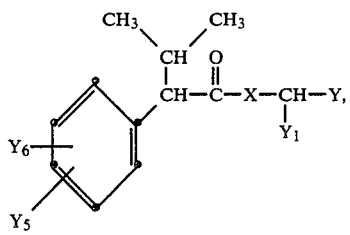

wherein X, Y and $Y_1$ are as defined for formula (3), $Y_5$ is hydrogen, $CH_3$, Cl, $NO_2$, $OCH_3$, $OCH(CH_3)_2$, —$OCH_2$C≡CH or —$OCH_2$CH=$CH_2$ and $Y_6$ is hydrogen, $CH_3$, Cl, Br or F or $Y_5$ and $Y_6$ in ortho-position together complete a fused benzene ring. It is preferred to use compounds of formula (3).

As particularly preferred components (B), there may be used such compounds of the above-defined formula (3) wherein Q is a radical of the formula

wherein $Y_3'$ is Br, Cl or $CH_3$, X is oxygen and Y is

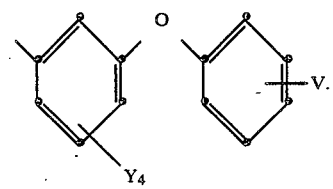

$Y_2$ in formula (3) is preferably $CH_3$ and $Y_1$ is hydrogen, CN, $CH_3$, —CH—$CH_2$, —C≡CH or —C≡C—$CH_3$, in particular hydrogen or CN.

In particularly useful compositions of the invention, component (B) is a compound selected from the class of 3"-phenoxybenzyl 3-(2',2'-dihalovinyl)-2,2-dimethylcyclopropanecarboxylates, in particular those of the formula

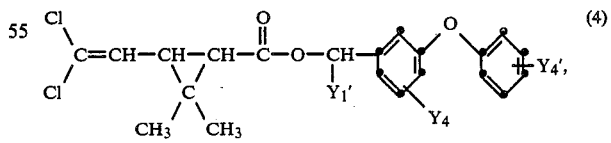

wherein $Y_1'$ is hydrogen, cyano, —CH=$CH_2$ or —C≡C—$CH_3$ and each of $Y_4$ and $Y_4'$ independently is hydrogen or fluorine. The common name of the compound of formula (4) wherein $Y_1'=Y_4=Y_4'$=hydrogen is permethrin, that of the compound wherein Y'=CN and $Y_4=Y_4'$=hydrogen is cypermethrin.

The compositions of the invention may consist exclusively of components (A) and (B) or they may additionally contain conventional carriers and formulation assistants such as solvents, water, acids, bases, surfactants, wetting agents, dispersants and/or emulsifiers.

Examples of suitable solvents are organic solvents such as aliphatic and alicyclic alcohols, ketones, hydrocarbons such as benzene, xylene, toluene, petroleum distillates, and chlorinated and fluorinated hydrocarbons, in particular propylene glycol, methoxyethanol, ethoxyethanol or dimethylformamide, if appropriate, in admixture with water.

Examples of further suitable formulation assistants are the conventional surface-active substances employed as wetting agents, dispersants and/or emulsifiers, e.g. those listed below as assistants for treatment baths in the process of this invention.

The compositions of the invention contain with particular advantage formulation ingredients which produce a storage stable, directly applicable formulation. Such formulation ingredients are described in European published application No. 74 335 (see components C to G). Accordingly, the present invention also relates to compositions which contain components (A) and (B) as well as components C to G described in the above European published application. The components described therein, their preferred representatives and their relative ratios constitute an object of the present invention.

The pyrethroids of formula (3) (component (B)) are known. In this connection, see e.g. the references to the literature on page 1. The 5-pyridyloxyphenylcarbamoyl)barbiturates of formula (1) can be obtained by methods which are known per se.

Compounds of formula (1) can for example be prepared by (a) reacting an ester of the formula

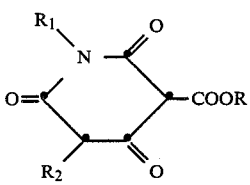  (5)

with an aniline derivative of the formula

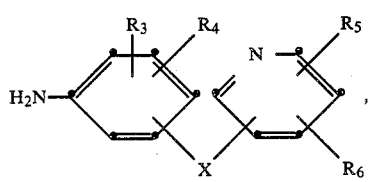  (6)

wherein R is an alkyl group or an unsubstituted or substituted phenyl group and the radicals $R_1$ to $R_6$ and X are as defined for formula (1), or (b) reacting a substituted barbituric acid of the formula

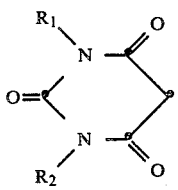  (7)

with a substituted phenylisocyanate of the formula

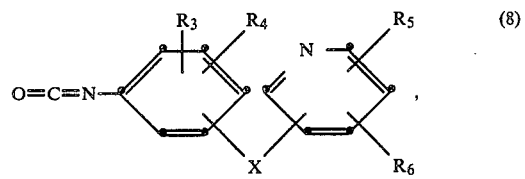  (8)

wherein the radicals $R_1$ to $R_6$ and X are as defined for formula (1), or (c) reacting a substituted barbituric acid of formula (7) with a substituted benzoylazide of the formula

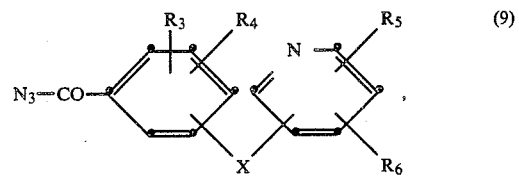  (9)

wherein the radicals $R_1$ to $R_6$ and X are as defined for formula (1).

Variants (a) and (c) are advantageously carried out at reaction temperatures in the range from 50° to 250° C., preferably from 70° to 220° C. Variant (b) necessitates reaction temperatures in the range from 0° to 220° C., preferably from 0° to 200° C. The reactions (a), (b) and (c) can be carried out under normal or increased pressure and in the absence or, preferably, in the presence of solvents or diluents. In some cases the reaction is advantageously carried out in the presence of a base.

Suitable solvents or diluents are e.g. ethers and ethereal compounds such as dialkyl ether (diethyl ether, diisopropyl ether, tert-butylmethyl ether etc.), anisole, dioxane, tetrahydrofuran; aliphatic and aromatic hydrocarbons such as benzene, toluene, petroleum ether; halogenated hydrocarbons such as chlorobenzene, methylene chloride, chloroform, ethylene chloride, carbon tetrachloride, tetrachloroethylene; nitriles such as acetonitrile, propionitrile; N,N,-dialkylated amides such as dimethylformamide; dimethylsulfoxide; ketones such as acetone, diethyl ketone, methyl ethyl ketone; and mixtures of such solvents.

Suitable bases are both organic and inorganic bases, e.g. tertiary amines such as trialkylamine (trimethylamine, triethylamine, tripropylamine etc.), pyridine and pyridine bases (e.g. 4-dimethylaminopyridine, 4-pyrrolidylaminopyridine etc.), picolines and lutidines as well as oxides, hydroxides, carbonates and bicarbonates of alkali metals and alkaline earth metals (e.g. CaO, BaO, NaOH, KOH, Ca(OH)$_2$, KHCO$_3$, NaHCO$_3$, Ca(HCO$_3$)$_2$, K$_2$CO$_3$, Na$_2$CO$_3$ etc.), and acetates such as CH$_3$COONa or CH$_3$COOK. Further suitable bases are alkalialcoholates such as sodium ethylate, sodium propylate, potassium tert-butylate or sodium methylate.

The amount of base advantageously added is 10 to 100% of the equimolar amount, based on the reactants.

In some cases it may be of advantage to carry out the reaction in an inert gas atmosphere. Suitable inert gases are e.g. nitrogen, helium, argon or carbon dioxide.

The starting materials indicated in variants (a), (b) and (c) are known (q.v. e.g. Chem. Ber. 54, 1038 [1921]) or they can be prepared in a manner analogous to that for preparing the known substances.

The 5-(pyridyloxyphenylcarbamoyl)barbituric acids of formula (1) and the preparation thereof are also described in European published application No. 135 155.

The preparation of compounds of formula (1) is also illustrated in the following preparatory Examples.

The ratio of the two active ingredients (A) and (B) in the compositions (active ingredient combinations) of the invention can vary within wide limits; it may be for example in the range from 10:1 to 1:10, preferably from 8:1 to 1:2. In particularly preferred compositions of the invention the ratio is about 1:1.

The compositions of the invention can be used for protecting keratinous material against insects that feed on keratin, e.g. against Lepidoptera larvae such as Tineola spec. and Tiena spec., and also Coleoptera larvae, e.g. Anthrenus spec. and Attagenus spec. The compositions are most suitable for proofing keratinous material against feeding damage by insects, especially for providing such material with a washfast and lightfast protective finish against insects, in particular moths and beetles. The keratinous material to be proofed can be both in the raw and in the processed state, for example raw or processed sheep's wool or products made of other animal hairs, hides, furs and feathers.

A particularly important feature is the effectiveness of the compositions of the invention against the larvae of the webbing clothes moth (*Tineola bisselliella*), the common clothes moth (*Tinea pellionella*) and of the false clothes moth (*Hofmannophila pseudopretella*), as well as against the larvae of fur beetles and carpet beetles (Attagenus spec. and Anthrenus spec. respectively), e.g. against larvae of *Anthrenus verbasci* and *Anthrenus pimpinellae*, of *Anthrenus scrophulariae*, of *Anthrenus fasciatus*, *Attagenus pellio* and, in particular, of the black fur beetle (*Attagenus piceus*) and of the carpet beetle (*Anthrenus vorax*).

The compositions of the invention are therefore preferably used on the one hand for protecting woollen textiles, for example blankets, wool carpets, woollen underwear, woollen clothing, knits and wool-containing textiles such as blends, one component of which is wool, for example blends of wool and other natural fibres, preferably cotton, or of wool and synthetic fibres, and, on the other hand, also for protecting furs and hides from attack by the above-mentioned pests.

The present invention also relates to a process for protecting keratinous material, in particular woollen textiles, from attack by pests that feed on keratin, e.g. moth and beetle larvae, which process comprises treating the material to be protected with a combination of one or more 5-(pyridyloxyphenylcarbamoyl)barbiturates of formula (1) and one or more synthetic pyrethroids, preferably of formula (3) and (3a). To this end, this active ingredient combination, which as composition of the invention may additionally contain conventional carriers and formulation assistants, is normally added to a treatment bath which may additionally contain conventional textile assistants and/or dyes, and the material to be protected is impregnated with said bath.

The two components (A) and (B) may of course be added to the treatment bath separately.

The materials to be protected, in particular textile materials, can be impregnated e.g. with hot or cold aqueous dye, bleaching, chroming or aftertreatment baths containing a specific amount of an active ingredient combination of the invention. Various textile finishing processes are possible, for example the pad or exhaust process.

The treatment is conveniently carried out in the temperature range from 10° to 100° C., in the dye bath preferably in the range from about 60° to 100° C. and in the aftertreatment or wash bath preferably in the range from 10° to 70° C., most preferably from 20° to 60° C.

As further assistants there may be added to the treatment baths e.g. dispersants, emulsifiers or surfactants provided that a sufficient amount thereof is not already present in the composition of the invention. The liquor can additionally contain further conventional assistants, such as water-soluble perborates, polyphosphates, carbonates, silicates, fluorescent whitening agents, softeners, salts with acid reaction, such as ammonium or zinc silicofluoride, or certain organic acids such as oxalic acid, acetic acid or, in particular, formic acid, and also antimicrobial agents and finishing agents, for example those bases on synthetic resins or starch. If the mothproof and beetleproof finishing is carried out together with the dyeing of the material (e.g. wool), the baths additionally contain the corresponding dyes and, if appropriate, the necessary assistants, e.g. levelling agents.

The aqueous treatment baths contain, for example, surfactants, for example anionic compounds, such as soaps and other carboxylates (e.g. alkali metal salts of higher fatty acids), derivatives of sulfur oxyacids (e.g. the sodium salt of dodecylbenzenesulfonic acid, water-soluble salts of sulfuric acid monoesters of higher molecular alcohols or of their polyglycol ethers, for example soluble salts of dodecyl alcohol sulfate or of dodecyl alcohol polyglycol ether sulfate), derivatives of phosphorus oxyacids (e.g. phosphates), derivatives with acid (electrophilic) nitrogen in the hydrophilic group (e.g. disulfine salts), cationic surface-active agents, such as amines and their salts (e.g. lauryldiethylenetriamine), onium compounds, amine oxides or nonionic surface-active agents, such as polyhydroxy compounds, surface-active agents based on mono- or polysaccharides, higher molecular acetylene glycols, polyglycol ethers (e.g. polyglycol ethers of higher fatty alcohols, polyglycol ethers of higher molecular alkylated phenols).

If non-aqueous application is made (solvent application), an appropriate amount of a composition (active ingredient combination) of the invention may also be added to a suitable solvent and the material to be protected may be impregnated with the solution so obtained. Suitable solvents for this application are, inter alia, trichloroethylene, methylene chloride, hydrocarbons, propylene glycol, methoxyethanol, ethoxyethanol, dimethylformamide, to which dispersants (e.g. emulsifiers, such as sulfated castor oil, fatty alcohol sulfates etc.) and/or other assistants can be added. The material to be protected is usually simply impregnated with these solutions.

The proofing of the material to be protected may also be combined with a dry cleaning process. To this end, an appropriate amount of a composition (active ingredient combination) of the invention is dissolved in the cleaning agent (such as a halogenated lower alkane, e.g.

trichloroethylene etc.) and the cleaning process is carried out in the usual manner.

However, an amount of a composition (active ingredient combination) of the invention may also be dissolved in a readily volatile solvent and the resultant solution then sprayed onto the substrate to be protected (spray application).

Wool-containing textile fabrics, furs and feathers are particularly suitable for this application. The advantage of the spray application is that pollution of the wastewaters is avoided on account of the recovery of the solvent.

In the process of the present invention, the compositions of the invention may also be used in combination with other protectants which act against insects that feed on keratin, for example with urea derivatives, benzimidazoles, aromatic sulfonamides and phosphoric and phosphonic acid esters.

The amount of a composition (active ingredient combination) which is added to the treatment bath or non-aqueous solvent depends on the substrate and the method of application. However, this amount is ordinarily such that, after application to the material which it is desired to protect, the latter contains about 10 to 2000 ppm, preferably 100 to 1000 ppm, of the active ingredient combination, namely of barbiturate and pyrethroid (components (A)+(B)), with the upper limit being largely determined by economic considerations, whereas the lower limit depends on criteria such as the intended breadth and permanency of the protective action. This corresponds, for example, to concentrations of 0.001 to 1 g of active ingredient per liter of treatment bath using exhaust process at a liquor to goods ratio of 1:20, depending on the degree of exhaustion attainable. In the pad process concentrations of up to 2 g of active ingredient per liter are possible.

In the following preparatory methods and Examples, parts and percentages are by weight unless otherwise stated. The term "permethrin" will be understood as meaning the above-defined compound of formula (4), wherein $Y_1'=Y_4=Y_4'=$hydrogen, and the term "cypermethrin" will be understood as meaning the compound of the above-defined formula (4), wherein $Y_1'=CN$ and $Y_4=Y_4'=$hydrogen.

Preparatory methods for a number of 5-(pyridyloxy-phenylcarbamoyl)barbituric acids of formula (1):

1. 1.60 g (0.007 mol) of 1,3-dimethyl-5-ethoxycarbonylbarbituric acid and 1.78 g (0.007 mol) of 4-(5-trifluoromethylpyrid-2-yloxy)aniline are suspended in 20 ml of toluene. The suspension is heated to reflux for 16 hours, during which time ethanol escapes. After cooling, the precipitate is isolated by filtration, washed with toluene and dried, affording 1,3-dimethyl-5-[4-(5-trifluoromethylpyrid-2-yloxy)phenylcarbamoyl]barbituric acid of the formula

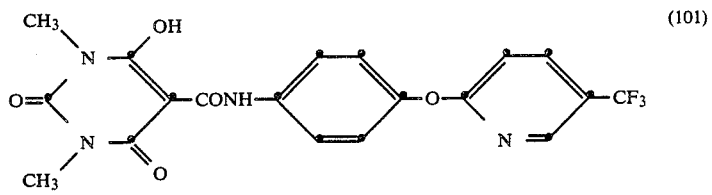

with a melting point of 180°–181° C.

2. 7.8 g (0.05 mol) of 1,3-dimethylbarbituric acid and 14 g (0.05 mol) of 4-(3,5-dichloropyrid-2-yloxy)-phenylisocyanate are suspended in 50 ml of xylene. 1 g of triethylamine is added dropwise to the suspension and the temperature rises to 45°–50° C. After further addition of 50 ml of xylene the mixture is stirred for 18 hours at this temperature. Then ⅓ of the xylene is distilled off. After cooling, the precipitate is isolated by filtration, washed with xylene, suspended several times in HCl and the suspension is thoroughly washed with water and dried, affording 1,3-dimethyl-5-[4-(3,5-dichloropyrid-2-yloxy)phenylcarbamoyl]barbituric acid of the formula

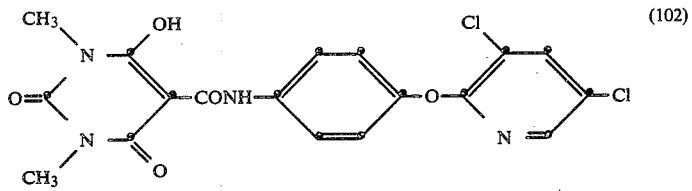

with a melting point of 234°–235° C.

The compounds of the formulae

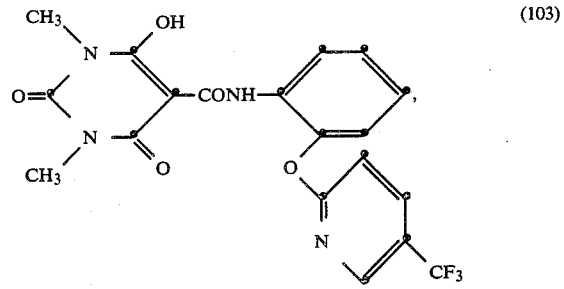

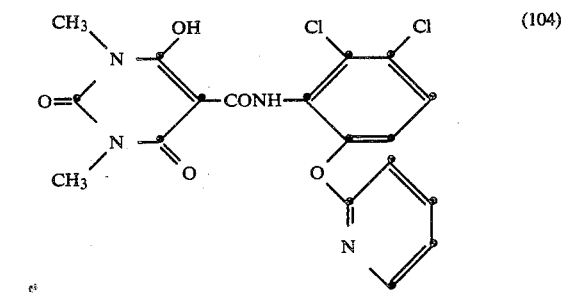

melting point: 241°–242° C., and

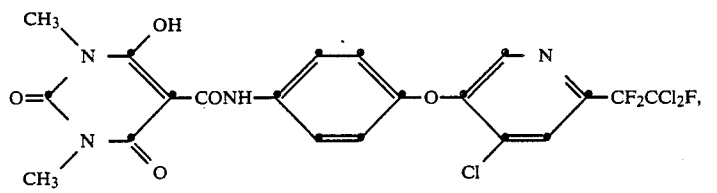

(105)

and the compounds of the formula

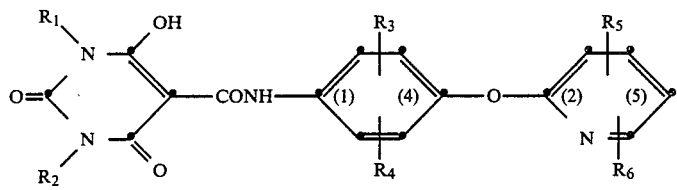

listed in the following Table 1 can be obtained by a procedure analogous to that described in preparatory methods 1 or 2 by using the corresponding starting materials.

the relative loss in weight of the test sample and, on the other, according to the number of still living organisms.

The tested active ingredient mixture exhibits an excellent action against all three pests at each concentration applied.

TABLE 1

| Compound | $R_1$ | $R_2$ | $R_3$ | $R_4$ | $R_5$ | $R_6$ | Melting point (°C.) |
|---|---|---|---|---|---|---|---|
| 106 | $CH_3$ | $CH_3$ | 3-Cl | 5-Cl | 3-Cl | 5-$CF_3$ | 205–206 |
| 107 | $CH_3$ | $CH_3$ | 3-Cl | 5-Cl | 5-$CF_3$ | H | 232–233 |
| 108 | $CH_2-CH=CH_2$ | $CH_3$ | H | H | 5-$CF_3$ | H | 105–107 |
| 109 | cyclopropyl | $CH_3$ | H | H | 5-$CF_3$ | H | 142–144 |
| 110 | $CH_3$ | $CH_3$ | 3-Cl | H | 3-Cl | 5-$CF_2CCl_2F$ | |
| 111 | $CH_3$ | $CH_3$ | H | H | 3-Cl | 5-$CF_2CClF_2$ | |
| 112 | $CH_3$ | $CH_3$ | 2-$CH_3$ | 6-$CH_3$ | 3-Cl | 5-$CF_3$ | |
| 113 | $CH_3$ | $CH_3$ | 2-$CH_3$ | 6-$CH_3$ | 3-Cl | 5-Cl | 251–253 |

EXAMPLE 1

A 0.4% stock solution of a 1:1 mixture of the compound of formula (101) and permethrin is ethylene glycol monomethyl ether is prepared. Then aqueous treatment baths containing, in 120 ml of distilled water, 0.12 ml of a wetting agent and dispersant, 0.6 ml of formic acid 1:10 and 0.2 ml, 0.1 ml and 0.05 ml respectively of the 0.4% stock solution, are prepared at room temperature. Then 3 g of wool flannel are wetted with hot water and put into the bath at room temperature. While constantly circulating the wool sample, the bath temperature is raised to 98° C. in the course of 20 minutes and treatment is carried out for 60 minutes at 98° C. The bath is then cooled, the wool sample rinsed twice for 3 minutes with distilled water, squeezed out by hand and dried in the air. The active ingredient concentration is 250, 125 or 60 ppm respectively, based on the weight of the wool.

The dried sample ist subjected to the mothproofing test (protection against feeding damage caused by the webbing clothes moth *Tineola biselliella* Hum.) and to the resistance test against larvae of the fur beetle (*Attagenus piceus* Oliv.) and carpet beetle (*Anthrenus vorax* Wat.) in accordance with Swiss standards. In these tests, 4-week-old larvae of *Tineola biselliella* and *Anthrenus vorax* and 6- to 7-week-old larvae of Attagenus piceus are used. Pieces of the same size are cut out of the treated wool samples and subjected for 14 days at constant temperature (28° C.) and constant relative humidity (65%) to attack (feeding) by 15 larvae of each of the pests. Evaluation is made on the one hand according to Fabrics with a complete mothproof and beetleproof finish are also obtained by repeating the above procedure using a 1:1 mixture of the compound of formula (101) and cypermethrin, 4-fluoro-3-phenoxy-α-cyanobenzyl 3-(2,2-dichlorovinyl)-2,2-dimethylcyclopropanecarboxylate (=compound 201) or 3-phenoxy-α-propin-1-ylbenzyl 3-(2,2-dichlorovinyl)-2,2-dimethylcyclopropanecarboxylate (=compound 202), or a 1:1 mixture of the compound of formula (102) and permethrin, cypermethrin, compound 201 or compound 202.

Excellent protective action against moth and beetle larvae is also obtained in the described finishing process by using as barbiturate component in the above-described compositions (active ingredient mixtures) one or more of the compounds of the formulae (103) to (113) in place of the compound of formula (101) or (102).

EXAMPLE 2

In the finishing process according to Example 1, the pyrethroid component (component (B)) may be one or more of the following compounds:

3-phenoxy-α-vinylbenzyl and 3-phenoxy-α-methylethinylbenzyl 3-(2,2-dichlorovinyl)-2,2-dimethylcyclopropanecarboxylate, 4-fluoro-3-phenoxybenzyl and 4-fluoro-3-phenoxy-α-cyanobenzyl 3-(2-methylpropen-1-yl)-2,2-dimethylcyclopropanecarboxylate, 4-fluoro-3-phenoxybenzyl and 4-fluoro-3-phenoxy-α-ethinylbenzyl 3-(2,2-dichlorovinyl)-2,2-dimethylcyclopropanecarboxylate, 4-fluoro-3-phenoxybenzyl, 4-fluoro-3-phenoxy-α-cyanobenzyl and 4-fluoro-3-phenoxy-α-ethinylbenzyl 3-(2,2-dibromovinyl)-2,2-dimethylcyclopropanecarboxylate, 4-fluoro-3-(4-fluorophenoxy)-α-cyanobenzyl 3-(2-methylpropen-1-yl)-2,2-dimethylcyclopropanecarboxylate, 4-fluoro-3-(3-fluorophenoxy)benzyl, 4-fluoro-3-(3-fluorophenoxy)-α-cyanobenzyl, 4-fluoro-3-(4-fluorophenoxy)benzyl and 4-fluoro-3-(4-fluorophenoxy)-α-cyanobenzyl 3-(2,2-dichlorovinyl)-2,2-dimethylcyclopropanecarboxylate, 4-fluoro-3-(3-fluorophenoxy)benzyl, 4-fluoro-3-(3-fluorophenoxy)-α-cyanobenzyl and 4-fluoro-3-(4-fluorophenoxy)-α-cyanobenzyl 3-(2,2-dibromovinyl)-2,2-dimethylcyclopropanecarboxylate, 4-fluoro-3-phenoxy-α-cyanobenzyl 3-(2-chloro-2-(4-chlorophenyl)-vinyl)-2,2-dimethylcyclopropanecarboxylate, 2- or 3-fluoro-3-(3- or 4-fluorophenoxy-α-cyanobenzyl 3-(2,2-dichlorovinyl)-2,2-dimethylcyclopropanecarboxylate, and/or one or more compounds of the following formulae:

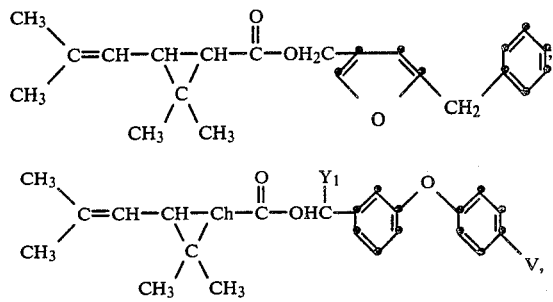

wherein
V=H, Cl, Br, F, CH₃ or NO₂ and
Y₁=H, CN, CH₃, C₂H₅, i—C₃H₇,

—C≡CH, —C≡C—CH₃, —CH=CH₂, —CH=CH—CH₃, —CH₂—CH=CH₂ or —CH₂—CH=CHCl;

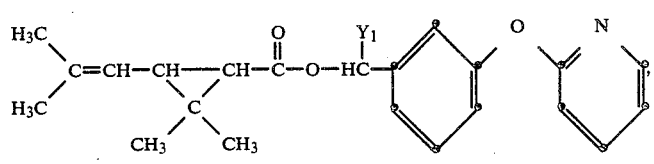

wherein
Y₁=H, CN or CH₃;

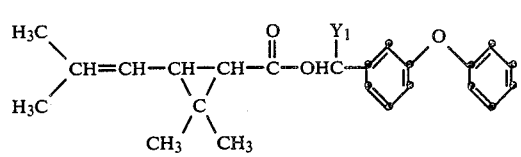

wherein
Y₁=H, CN or —C≡CH;

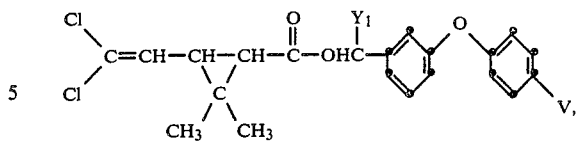

wherein
V=H, Cl, Br, F, CH₃ or NO₂ and
Y₁=H, CN, CH₃, C₂H₅, i—C₃H₇, $$-\underset{\underset{Br}{|}}{\overset{\overset{}{|}}{C}}=CH,\ Br$$

—C≡CH, —C≡C—CH₃, —CH=CH₂, —CH=CH—CH₃, —CH₂—CH=CH₂, —CH₂—CH=CHCl or —C≡C—C₆H₅;

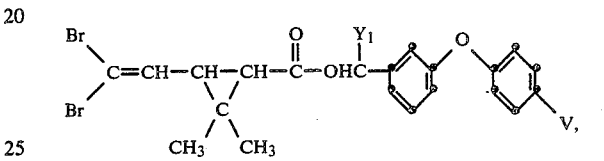

wherein
V=H, Cl, Br, F, CH₃ or NO₂ and
Y₁=H, CN, CH₃, C₂H₅, i—C₃H₇, $$-\underset{\underset{Br}{|}}{\overset{\overset{}{|}}{C}}=CH,\ Br$$

—C≡CH, —C≡C—CH₃, —CH=CH₂, —CH=CH—CH₃, —CH₂—CH=CH₂, —CH₂—CH=CHCl or —C≡C—C₆H₅;

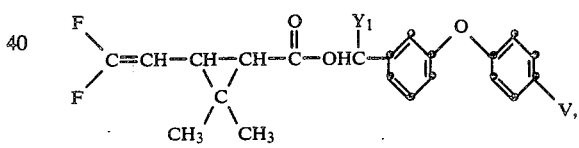

wherein
V=H, Cl, Br, F, CH₃ or NO₂ and
Y₁=H, CN, CH₃, C₂H₅, i—C₃H₇,

—C≡CH, —C≡C—CH₃, —CH=CH₂, —CH=CH—CH₃, —CH₂—CH=CH₂, —CH₂—CH=CHCl or —C≡C—C₆H₅;

$V_1 =$ —$CH_2$—CH=$CH_2$, —$CH_2$—C≡CH, —$CH_2$—CH=CH—$CH_3$,
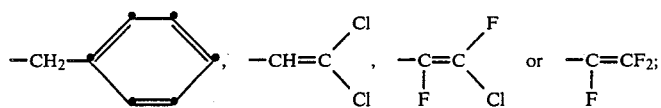
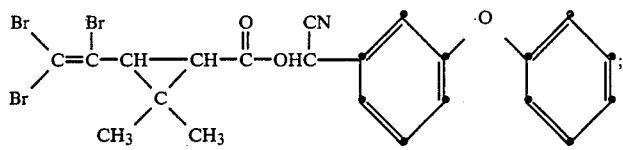
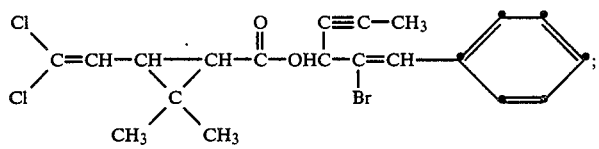
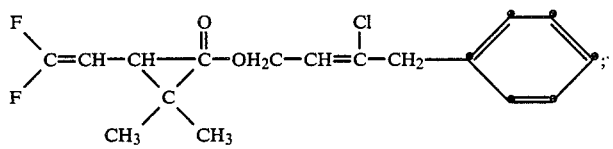
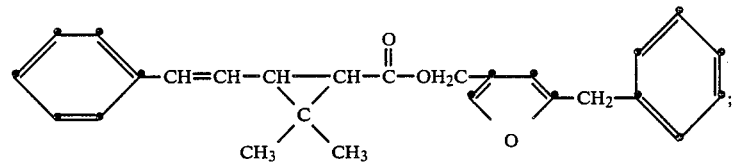
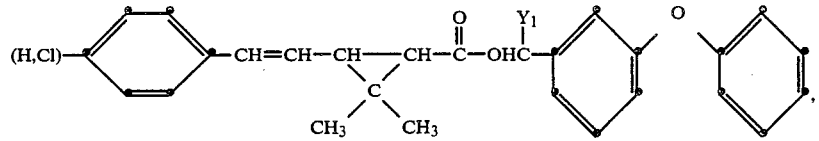
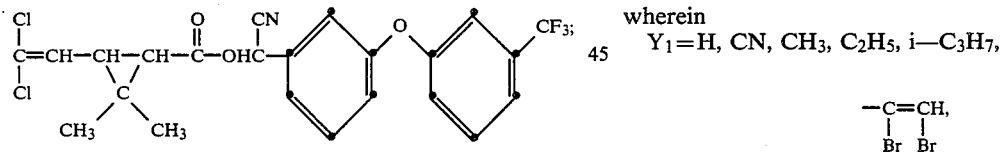
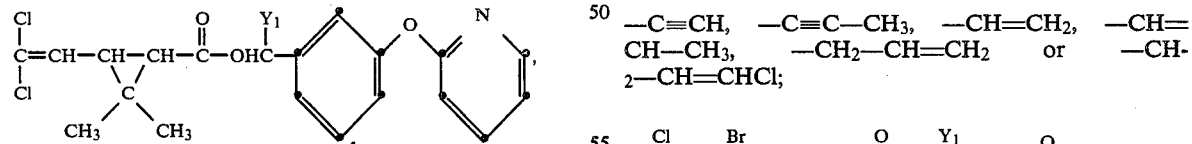
wherein
$Y_1 =$ H, CN or $CH_3$;
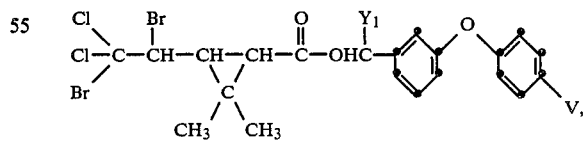
wherein
$Y_1 =$ H, CN or $CH_3$ and
wherein
$Y_1 =$ H, CN, $CH_3$, $C_2H_5$, i—$C_3H_7$,
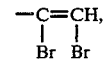
—C≡CH, —C≡C—$CH_3$, —CH=$CH_2$, —CH=CH—$CH_3$, —$CH_2$—CH=$CH_2$ or —$CH_2$—CH=CHCl;
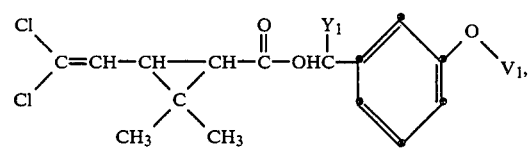
wherein
V = H, Cl, Br, F, $CH_3$ or $NO_2$ and
$Y_1 =$ H, CN, $CH_3$, $C_2H_5$, i—$C_3H_7$,
—C=CH,
 |   |
 Br  Br —C≡CH, —C≡C—CH₃, —CH=CH₂, —CH=CH—CH₃, —CH₂—CH=CH₂ or —CH₂—CH=CHCl;

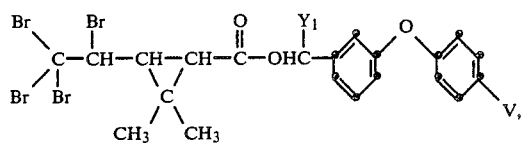

wherein
  V=H, Cl, Br, F, CH₃ or NO₂ and
  $Y_1$=H, CN, CH₃, C₂H₅, i—C₃H₇, $$-\underset{\underset{Br}{|}}{\overset{\overset{Br}{|}}{C}}=CH,$$

—C≡CH, —C≡C—CH₃, —CH=CH—CH₃, —CH₂—CH=CH₂ or —CH₂—CH=CHCl;

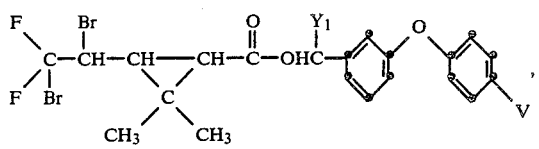

wherein
  V=H, Cl, Br, F, CH₃ or NO₂ and
  $Y_1$=H, CN, CH₃, C₂H₅, i—C₃H₇, $$-\underset{\underset{Br}{|}}{\overset{\overset{Br}{|}}{C}}=CH,$$

—C≡CH, —C≡C—CH₃, —CH=CH—CH₃, —CH₂—CH=CH₂ or —CH₂—CH=CHCl;

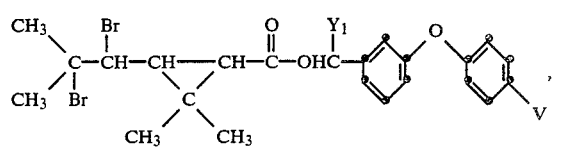

wherein
  V=H, Cl, Br, F, CH₃ or NO₂ and
  $Y_1$=H, CN, CH₃, C₂H₅, i—C₃H₇, $$-\underset{\underset{Br}{|}}{\overset{\overset{Br}{|}}{C}}=CH,$$

—C≡CH, —C≡C—CH₃, —CH=CH—CH₃, —CH₂—CH=CH₂ or —CH₂—CH=CHCl;

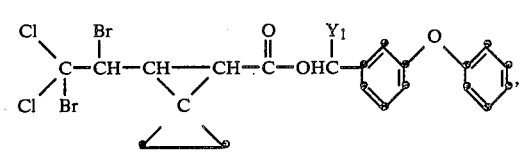

wherein
  $Y_1$=H or CN;

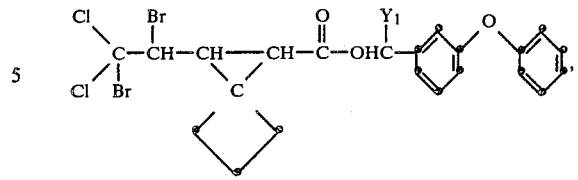

wherein
  $Y_1$=H or CN;

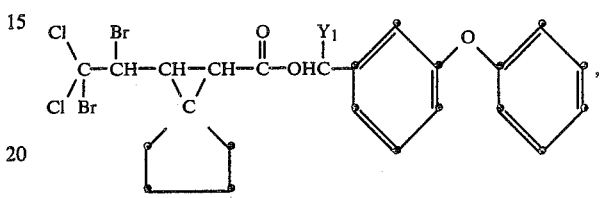

wherein
  $Y_1$=H or CN;

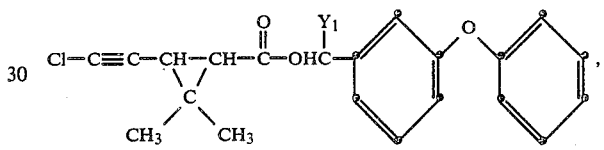

wherein
  $Y_1$=H, CN or —CH=CH—CH₃;

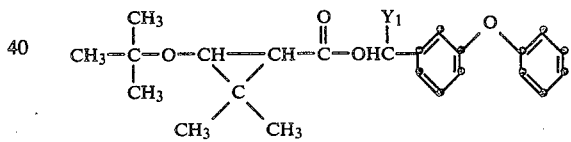

wherein
  $Y_1$=H or CN;

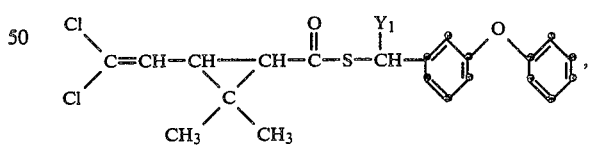

wherein
  $Y_1$=H, CH₃ or CN;

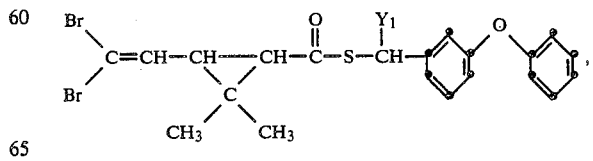

wherein
  $Y_1$=H or CH₃;

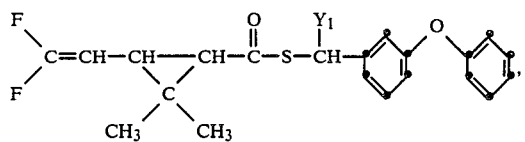
wherein
X=H or CH₃;
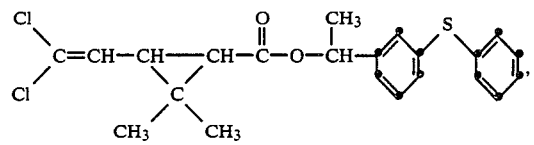
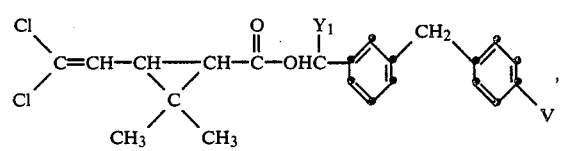
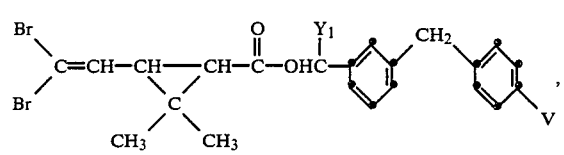
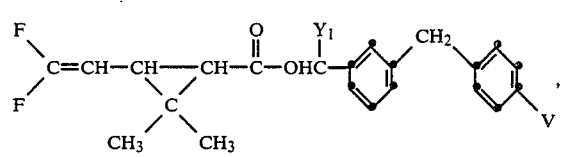
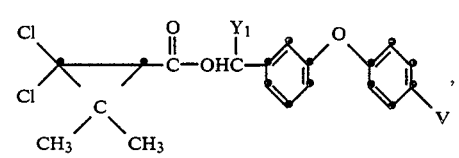
in each of which formulae
V=H, Cl, Br, F, CH₃ or NO₂ and
Y₁=H, CN, CH₃, C₂H₅, i—C₃H₇,
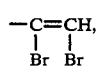
—C≡CH, —C≡C—CH₃, —CH=CH₂, —CH=CH—CH₃, —CH₂—CH=CH₂, —CH₂—CH=CHCl or —C≡C—C₆H₅;
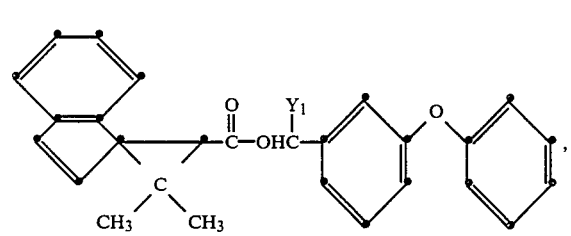
wherein
Y₁=H, CN, CH₃ or —C≡C—CH₃;
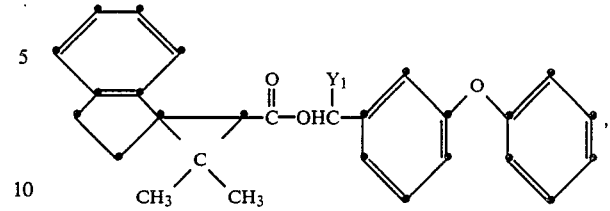
wherein
Y₁=H, CN, CH₃ or —C≡C—CH₃;
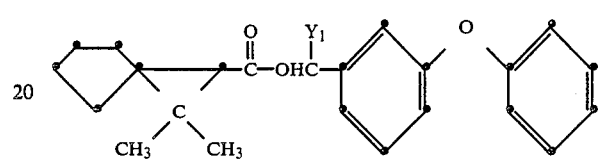
wherein
Y₁=H, CN, CH₃ or —C≡C—CH₃;
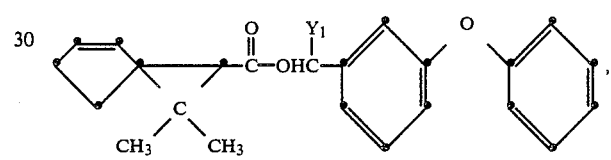
wherein
Y₁=H, CN, CH₃ or —C≡C—CH₃;
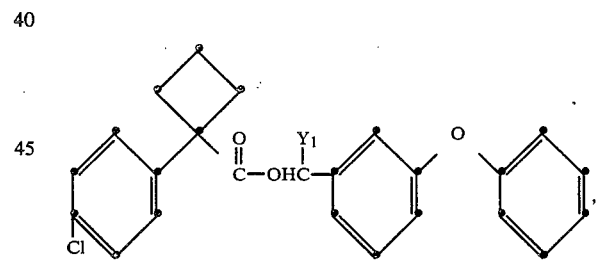
wherein
Y₁=H, CN or —C≡CH;
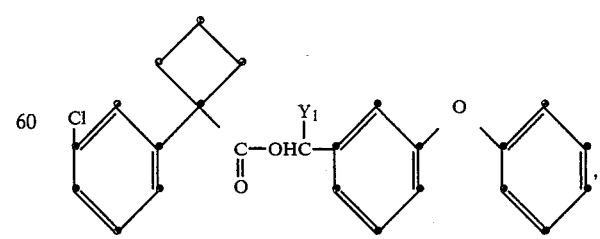
wherein
Y₁=H or CN;

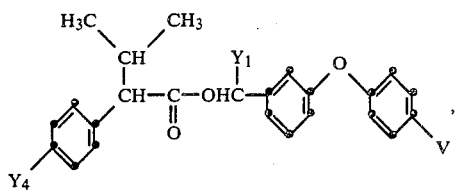

wherein
V=H, Cl, Br, F, CH₃ or NO₂ and
Y₁=H, CN, CH₃, C₂H₅, i—C₃H₇,

—C≡CH, —C≡C—CH₃, —CH=CH₂, —CH=CH—CH₃, —CH₂—CH=CH₂, —CH₂—CH=CHCl or —C≡C—C₆H₅ and
Y₄=H, CH₃, Cl, NO₂, CN, —OCH₃,

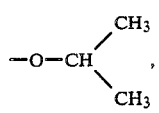

—O—CH₂—C≡CH or —O—CH₂—CH=CH₂;

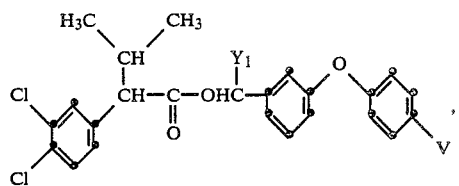

wherein
V=H, Cl, Br, F, CH₃ or NO₂ and
Y₁=H, CN, CH₃, C₂H₅, i—C₃H₇,

—C≡CH, —C≡C—CH₃, —CH=CH₂, —CH=CH—CH₃, —CH₂—CH=CH₂ or —CH₂—CH=CHCl;

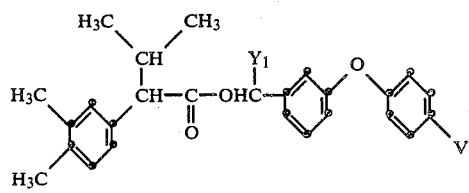

wherein
V=H, Cl, Br, F, CH₃ or NO₂ and
Y₁=H, CN, CH₃, C₂H₅, i—C₃H₇,

—C≡CH, —C≡C—CH₃, —CH=CH₂, —CH=CH—CH₃, —CH₂—CH=CH₂ or —CH₂—CH=CHCl;

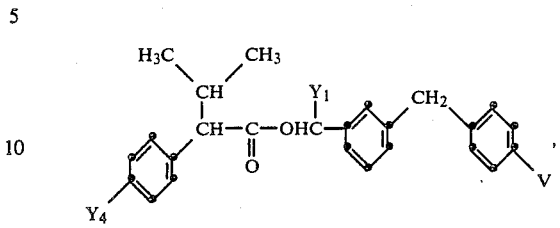

wherein
V=H, Cl, Br, F, CH₃ or NO₂ and
Y₁=H, CN, CH₃, C₂H₅, i—C₃H₇,

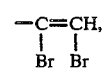

—C≡CH, —C≡C—CH₃, —CH=CH₂, —CH=CH—CH₃, —CH₂—CH=CH₂ or —CH₂—CH=CHCl and
Y₄=H, CH₃, Cl, NO₂, CN, —OCH₃,

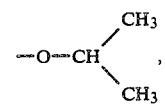

—OCH₂—C≡CH or —O—CH₂—CH=CH₂;

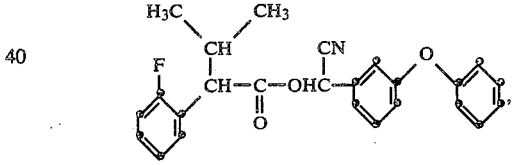

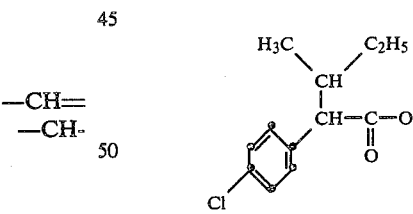

wherein
Y₁=H or CN;

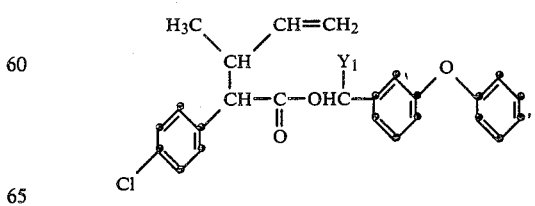

wherein
Y₁=H or CN;

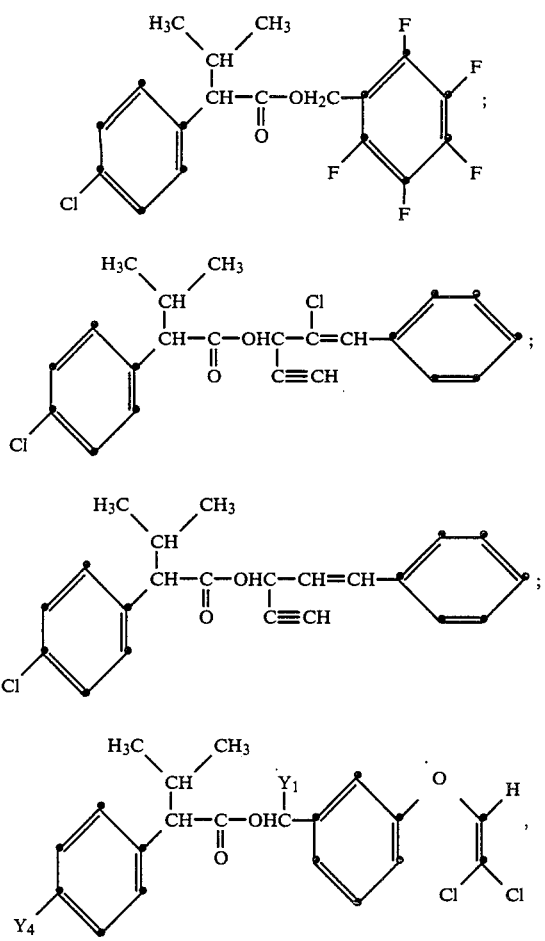
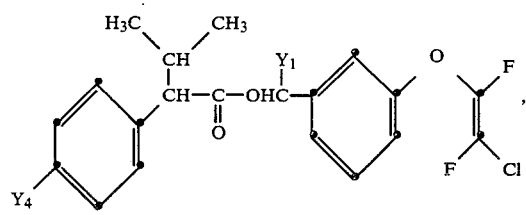
wherein
$Y_1 = H$, CN or $CH_3$ and
$Y_4 = H$ or Cl;
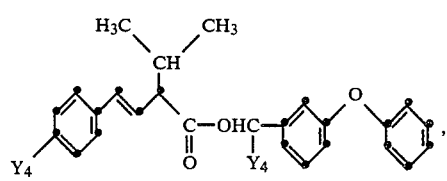
wherein
$Y_1 = H$, CN or $CH_3$ and
$Y_4 = H$ or Cl;
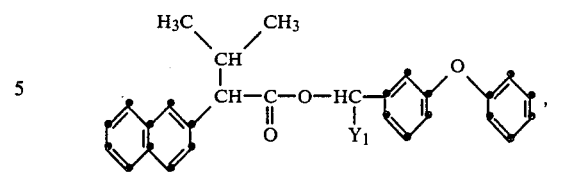
wherein
$Y_1 = H$ or CN;
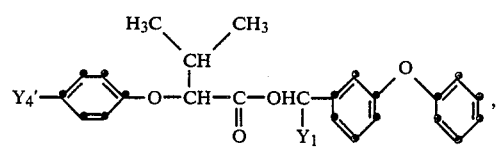
wherein
$Y_1 = H$ or CN and
$Y_4' = Cl$, $CH_3$ or H;
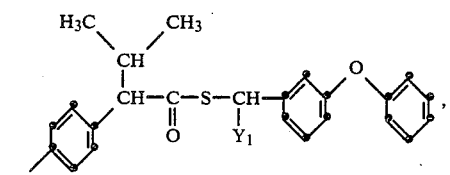
wherein
$Y_1 = H$, $CH_3$, $-C\equiv CH$ or CN;
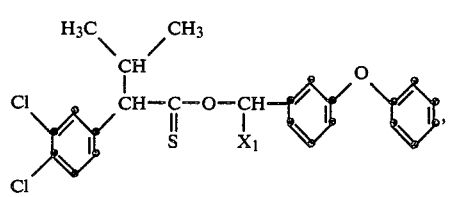
wherein
$Y_1 = H$ or CN;
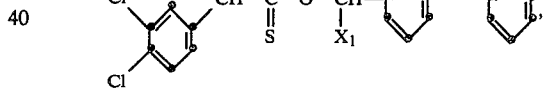
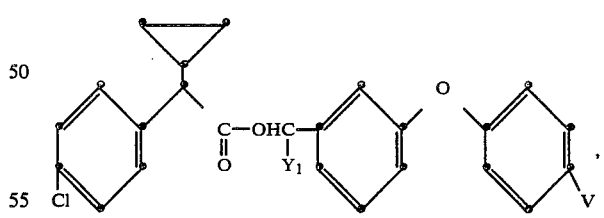
wherein
V = H, Cl, Br, F, $CH_3$ or $NO_2$ and
$Y_1 = H$, CN, $CH_3$, $C_2H_5$, i—$C_3H_7$,
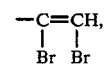
—C≡CH, —C≡C—$CH_3$, —CH=$CH_2$, —CH=CH—$CH_3$, —$CH_2$—CH=$CH_2$ or —$CH_2$—CH=CHCl.
wherein
$Y_1 = H$, CN or $CH_3$ and
$Y_4 = H$ or $CH_3$;

EXAMPLE 3

A 0.4% stock solution of a 1:1 mixture of the compound of formula (101) and permethrin in ethylene glycol monomethyl ether is prepared. The stock solution (12.5 ml) is diluted to 50 ml (solution 1) with ethylene glycol monomethyl ether which contains 0.65 g/l of a wetting agent and dispersant. Solution 1 (25 ml) is then diluted to 50 ml (solution 2) with ethylene glycol monomethyl ether which contains 0.5 g/l of a wetting agent and dispersant. Solution 2 (25 ml) is diluted in turn to 50 ml (solution 3) with ethylene glycol monomethyl ether which contains 0.5 g/l of a wetting agent and dispersant.

3 ml of each of solutions 1, 2 and 3 are poured into crystallisation dishes and a disc of wool flannel is wetted for 3 seconds therein. The moist discs are then padded between aluminium sheets to a pick-up of 50% of each solution. The concentrations of active ingredient are, respectively, 500 ppm, 250 ppm and 125 ppm for the discs treated with solutions 1, 2 and 3. The discs are then dried in the air and subjected to the same biological tests as in Example 1.

The tested active ingredient mixture exhibits an excellent action against all three pests at each concentration applied.

Fabrics with a complete mothproof and beetleproof finish are also obtained by repeating the above procedure using a 1:1 mixture of the compound of the formula (101) and cypermethrin or compound 201 or 202, or another active ingredient combination indicated in Example 1, or a further active ingredient combination of the invention obtained according to Examples 1 and 2.

EXAMPLE 4

A 10% solution of a 1:1 mixture of the compound of formula (101) and permethrin in ethylene glycol monomethyl ether is prepared. One part by volume of this solution is diluted with 200 parts by volume of a solvent suitable for dry cleaning, for example a suitable petroleum fraction or perchloroethylene. If desired, cleaning promoters can be added. Woollen articles are then treated in the conventional manner in this cleaning fluid and subsequently centrifuged to a solvent pick-up of about 100% of the weight of the wool. After drying, the articles have a good protective finish against the above-named pests that feed on keratin.

EXAMPLE 5

A 0.5% solution of a 1:1 mixture of the compound of formula (102) and permethrin in methylene chloride, trichloroethylene or a low boiling petroleum fraction is prepared. A woollen article is sprayed with this solution from a conventional spray device, so that $2\times 15$ g/m$^2$ of active ingredient solution is applied, corresponding to a concentration of about 400 ppm of the active ingredient combination on the material at a 30% consumption of the aerosol. The treated woollen fabric has a good protective finish against the above-named pests that feed on keratin.

Fabrics with a protective finish against attack by insects that feed on keratin are also obtained by repeating the procedure described in Examples 4 and 5 using a 1:1 mixture of the compound of formula (101) and cypermethrin or compound 201 or 202, or another active ingredient combination indicated in Example 1, or a further active ingredient combination of the invention obtained from Examples 1 and 2.

If the active ingredient combinations of the invention are not added direct to the treatment baths, then said combinations may also be formulated by adding different carriers, solvents and/or assistants. Particularly advantageous storage stable formulations are obtained by formulating the two components of the invention in the manner indicated in European published application 74 335, i.e. by preparing a formulation which, in addition to containing the two components (A) and (B), contains one or more aliphatic or cycloaliphatic amines and/or amides or derivatives thereof and, if appropriate, one or more organic solvents, water, one or more surfactants and/or emulsifiers or dispersants and/or one or more aliphatic carboxylic acids. The active ingredient combinations of the invention may also be formulated as described in Examples 1 to 25 of the above-mentioned European published application No. 74 335. The following two formulations shall serve as Examples:

EXAMPLE 6

5.3 parts of permethrin,
8.0 parts of 1-hydroxyethyl-2-oleylimidazoline,
7.0 parts of tallow fatty amine ethoxylated with 6–7 mol of ethylene oxide,
73.7 parts of diethylene glycol ethyl ether and
1.0 part of racemic lactic acid,
are mixed. With constant stirring, 5.0 parts of the compound of formula (102) are added at 45°–55° C. to this mixture until a homogenous formulation is obtained. The resultant mothproofing formulation is storage stable, water-miscible and, when applied to keratinous material, gives excellent mothproof and beetleproof finishes.

EXAMPLE 7

The formulation of the following composition is obtained in a manner analogous to that of Example 6:
5.5 parts of permethrin,
5.0 part of the compound of formula (101),
20.0 parts of tallow fatty amine ethoxylated with 6–7 mol of ethylene oxide,
5.0 parts of a block polymer of propylene glycol and ethylene oxide (mean molecular weight: 4900; 80% hydrophobic groups, 20% hydrophilic groups; HLB=4),
7.0 parts of castor oil polyglycol ether,
3.0 parts of a partial alkyl ester of phosphoric acid,
54.5 parts of isophoron (=3,5,5-trimethyl-2-cyclohexen-1-one).

EXAMPLE 8

The formulation of the following composition is obtained in a manner analogous to that of Example 6:
5.5 parts of permethrin,
5.0 parts of the compound of formula (101),
45.0 parts of the compound of the formula

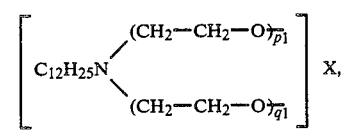

wherein $p_1+q_1=8$ and X is an acid phosphoric acid radical, 20.0 parts of a block polymer of propylene glycol and ethylene oxide (mean molecular weight: 6350; 50% hydrophobic and 50% hydrophilic groups; HLB=15), 12.5 parts of the sodium salt of nonylphenol ether sulfate ethoxylated with 40 mol of ethylene oxide, 7.0 parts of ethyl polyglycol, 5.0 parts of polyethylene glycol 300.

Advantageous storage stable formulations which can be used for providing keratinous material with a protective finish against attack by pests that feed on keratin are also obtained by using in the formulations of Examples 6–8 cypermethrin or compound 201 or 202 in place of permethrin or using another active ingredient combination indicated in Example 1 or a further active ingredient combination of the invention obtained from Examples 1 and 2 in place of permethrin and the compound of formula (101) or (102).

EXAMPLE 9

Dyeing and simultaneous mothproof and beetleproof finish: In a dyeing apparatus, a piece of wool fabric is prewetted for 5 minutes at 40° C. in 600 g of a dye liquor comprising 0.15 g of the formulation of Examples 6, 7 or 8,
30.3 g of Glauber's salt,
24.0 g of conc. sulfuric acid,
3.0 g of a red dye of the formula

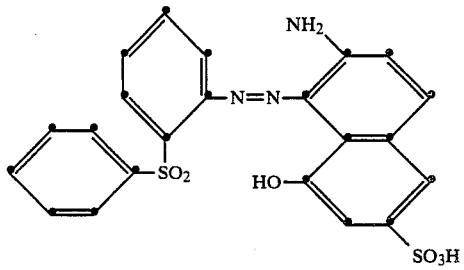

541.5 g of demineralised water.

The liquor to goods ratio is 1:20.

The liquor is then heated over 45 minutes to about 98° C. After it has been treated for 1 hour at this temperature, the wool fabric is rinsed and dried. The dye as well es the two active ingredients contained in each respective formulation have exhausted onto the fabric. After this single bath treatment, the red woollen fabric is fully protected against feeding damage by the larvae of moths and beetles. This is confirmed by the resistance test according to Swiss standards.

EXAMPLE 10

Application by aftertreatment bath: In a dyeing apparatus, a piece of wool fabric is prewetted for 5 minutes at 30° C. in 400 g of an aftertreatment bath comprising 1 g of the formulation of Example 6, 7 or 8, 4 g of 85% formic acid and 395 g of demineralised water.

The liquor to goods ratio is 1:20.

The bath is then warmed over 20 minutes to 45° C. and after it has been treated at this temperature for 30 minutes with constant agitation, the wool fabric is thoroughly rinsed in cold water and dried. The treated fabric is fully protected against the larvae of wool pests.

What is claimed is:

1. A composition for protecting keratinous material from attack by pests that feed on keratin, which composition contains (A) one or more 5-phenylcarbamoylbarbiturates of the formula

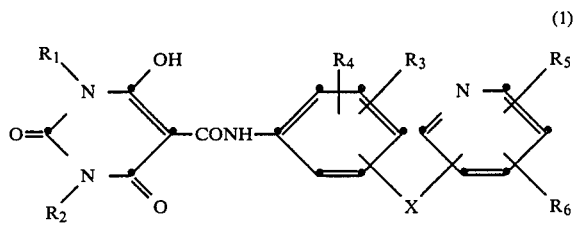

wherein each of $R_1$ and $R_2$ independently is $C_1$-$C_4$alkyl, $C_3$-$C_6$cycloalkyl, $C_2$-$C_4$alkenyl, benzyl, phenyl or phenyl substituted by 1 to 3 substituents selected from the group consisting of halogen, $C_1$-$C_4$alkyl, $C_1$-$C_4$alkoxy and nitro, each of $R_3$ and $R_4$ independently is hydrogen, halogen, $C_1$-$C_4$haloalkyl, $C_1$-$C_4$alkyl, $C_2$-$C_4$alkenyl, $C_3$-$C_6$cycloalkyl or methoxy, each of $R_5$ and $R_6$ independently is hydrogen, halogen, $C_1$-$C_4$alkyl, $C_1$-$C_4$haloalkyl or methoxy and X is oxygen or sulfur, or tautomeric forms or salts thereof, and (B) one or more synthetic pyrethroids.

2. A composition according to claim 1, wherein component (A) is a compound of formula (1), wherein X is oxygen and the pyridine ring is attached through the 2-position to the oxygen atom.

3. A composition according to claim 1, wherein component (A) is a compound of the formula

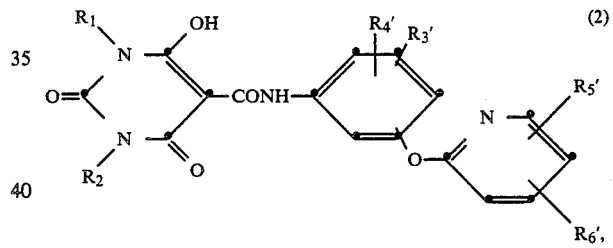

wherein $R_1$ and $R_2$ are as defined in claim 1 and each of $R_3'$, $R_4'$, $R_5'$ and $R_6'$ independently is hydrogen, halogen, $C_1$-$C_4$alkyl, $C_1$-$C_4$haloalkyl or methoxy, or a tautomeric form or salt thereof.

4. A composition according to claim 1 or 3, wherein component (A) is a compound of formula (1) or (2), wherein $R_1$ is methyl, ethyl, cyclopropyl or allyl, $R_2$ is ethyl or methyl, preferably methyl, each of $R_3$ and $R_4$ or each of $R_3'$ and $R_4'$ independently is hydrogen, halogen, or $C_1$-$C_4$alkyl and each of $R_5$ and $R_6$ or each of $R_5'$ and $R_6'$ independently is hydrogen, halogen, or $C_1$-$C_4$haloalkyl, and the substituent

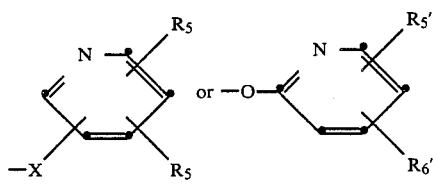

is in ortho- or para-position relative to the carbamoyl group.

5. A composition according to claim 4, wherein component (A) is a compound of formula (2), wherein $R_1$ is allyl or methyl, R₂ is methyl, each of R₃' and R₄' independently is hydrogen, chlorine or methyl and each of R₅' and R₆' independently is hydrogen, chlorine or trifluoromethyl.

6. A composition according to claim 5, wherein component (A) is a compound of formula (2), wherein the radical

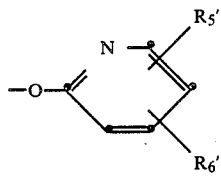

is in para-position relative to the carbamoyl group and R₅' is trifluoromethyl and R₆' is hydrogen.

7. A composition according to claim 1, wherein component (B) is a synthetic pyrethroid selected form the class of cyclopropanecarboxylates or α-alkylphenylacetates.

8. A composition according to claim 7, wherein component (B) is a pyrethroid of the general formula

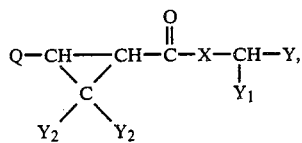

wherein
Q is Br₂C=Br—,

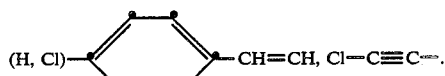

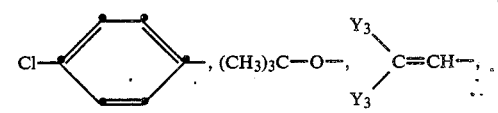

wherein Y₃ is Cl, Br, CF₃, F or C₁–C₄alkyl, CH₂=CH—CH₂—O— or

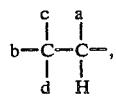

wherein each of a, b, c and d independently is Cl, Br or F, and c and d may also be methyl,
X is oxygen or sulfur,
Y₁ is hydrogen, CN, CH₃, C₂H₅, i—C₃H₇,

—C≡CH, —C≡C—CH₃, —C≡C—C₆H₅ —CH=CH—CH₃, —CH₂—CH=CH₂, —CH=CH₂ or —CH₂—CH=CHCl,
Y₂ is methyl or both substituents Y₂ together complete a cyclopropane, cyclobutane or cyclopentane ring, and Y is

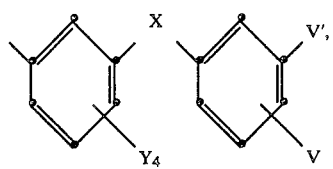

wherein Y₄ is hydrogen or fluorine and V is hydrogen, Cl, Br, F, CH₃ or NO₂ and V' is hydrogen, with the proviso that, when V is hydrogen, V' may also be CF₃, and X is as defined above; or Y is

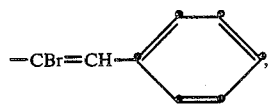

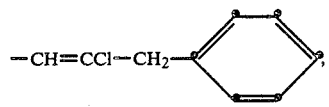

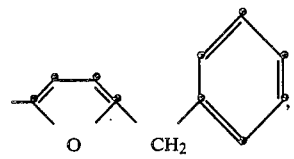

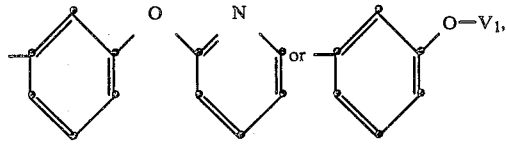

wherein V₁ is —CH₂—CH=CH₂, —CH₂—C≡CH,

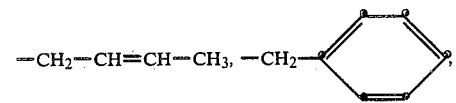

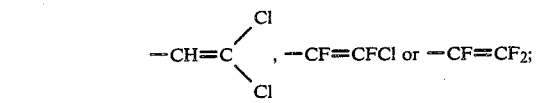

or of the general formula

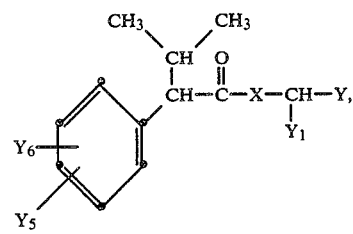

wherein X, Y and Y₁ are as defined for formula (3), Y₅ is hydrogen, CH₃, Cl, NO₂, OCH₃, OCH(CH₃)₂, —OCH₂C≡CH or —OCH₂CH=CH₃ and Y₆ is hydrogen, CH₃, Cl, Br or F or Y₅ and Y₆ in ortho-position together complete a fused benzene ring.

9. A composition according to claim 8, wherein component (B) is a pyrethroid of formula (3), wherein Q is a radical of the formula $$\begin{array}{c} Y_3' \\ \phantom{Y_3'}\diagdown \\ \phantom{Y_3'}\phantom{\diagdown}C=CH-, \\ \phantom{Y_3'}\diagup \\ Y_3' \end{array}$$

wherein $Y_3'$ is Br, Cl or $CH_3$, X is oxygen and Y is

[structure with Y4 and V substituents]

$Y_2$ is $CH_3$ and $Y_1$ is hydrogen, CN, $CH_3$, $-CH=CH_2$, $-C\equiv CH_2$, or $-C\equiv C-CH_3$.

10. A composition according to claim 1, which contains, in addition to components (A) and (B), conventional carriers and/or formulation assistants such as organic solvents, water, acids, bases, wetting agents, dispersants and/or emulsifiers.

11. A composition according to claim 10, which contains, in addition to components (A) and (B), one or more aliphatic or cycloaliphatic amines and/or amides or derivatives thereof and, if appropriate, one or more organic solvents, water, one or more surfactants and/or emulsifiers or dispersants, and/or one or more aliphatic carboxylic acids.

12. A composition according to claim 1, wherein the ratio of the two components (A) and (B) is in the range from 10:1 to 1:10.

13. A composition according to claim 12, wherein the ratio of the two components (A) and (B) is in the range from 8:1 to 1:2.

14. A process for providing keratinous material, with a protective finish against attack by pests that feed on keratin, which process comprises treating the material to be protected with an active ingredient combination containing one or more 5-phenylcarbamoylbarbiturates of formula (1) of claim 1, or tautomeric forms or salts thereof, and one or more synthetic pyrethroids.

15. A process according to claim 14, wherein in formula (1), X is oxygen, $R_1$ and $R_2$ are $C_1$-$C_4$alkyl or allyl, and the substituent

[structure with N, R5, R6 and -O- substituents]

is in ortho- or para-position relative to the carbamoyl group, and synthetic pyrethroids of formula (3), wherein Q is a radical of the formula $$\begin{array}{c} Y_3' \\ \phantom{Y_3'}\diagdown \\ \phantom{Y_3'}\phantom{\diagdown}C=CH-, \\ \phantom{Y_3'}\diagup \\ Y_3' \end{array}$$

wherein $Y_3'$ is Br, Cl or $CH_3$, X is oxygen and Y is

[structure with Y4 and V substituents]

and $Y_2$ is $CH_3$ and $Y_1$ is hydrogen, CN, $CH_3$, $-CH=CH_2$, $-C\equiv CH$ or 13 $C\equiv CH-CH_3$.

16. A process according to claim 14, which comprises using a composition which, in addition to the active ingredient combination, contains conventional carriers and/or formulation assistants.

17. A process according to claim 14, which comprises treating the material to be protected, by the exhaust or pad process, with an aqueous liquor which contains an active ingredient combination as defined in claim 14, and which aqueous liquor may additionally contain conventional textile assistants.

18. A process according to claim 14, which comprises spraying the material to be protected with an organic cleaning liquid containing an active ingredient combination as defined in claim 14.

19. A process according to claim 14, which comprises treating the material to be protected with an organic solvent containing an active ingredient combination as defined in claim 14.

20. A process according to claim 14, which comprises applying to the material to be protected the active ingredient combination in an amount of 10 to 2000 ppm, based on said material.

21. A process according to claim 14, which comprises treating woollen textiles in a dye bath by the exhaust process.

22. A process according to claim 14, which comprises treating woollen textiles in an aftertreatment bath by the exhaust process.

23. The keratinous material finished according to the process of claim 14.

24. The keratinous material finished according to claim 23, preferably wool-containing textiles, furs and hides containing 10 to 2000 ppm, preferably 100 to 1000 ppm, of an active ingredient combination as defined in claim 1.

25. The composition of claim 4 wherein $R_1$ is methyl, $R_2$ is methyl, each of $R_3$, $R_4$, $R_3'$, $R_4'$ and halogen are chlorine, and each of $R_5$, $R_6$, $R_5'$ and $R_6'$ halogen is chlorine and each of said $R_5$, $R_6$, $R_5'$, and $R_6'$ $C_1$-$C_4$ haloalkyl is $CF_3$.

26. The composition of claim 5 wherein $R_1$ is methyl.

27. The process of claim 14 wherein said keratinous material is selected from wool, fur, feathers, and hide.

28. The process of claim 15 wherein $R_1$ and $R_2$ are methyl or ethyl.

29. The process of claim 16 wherein said formulation assistants are organic solvents, water, acids, bases, wetting agents, dispersants and/or emulsifiers.

30. The process of claim 17 wherein said material to be protected is a textile containing wool fibers.

31. The process of claim 17 wherein said textile assistants are dispersants and/or dyes.

32. The process of claim 20 comprising applying said active ingredient combination in an amount of 100 to 1000 ppm based on said material.

33. A method of using the composition of claim 1 or 2 for protecting keratinous material against attack by pests that feed on keratin comprising treating said keratinous material with an anti-keratinous-material-feeding-pest amount of said composition.

34. The method of claim 33 wherein said keratinous material is a woolen textile.

* * * * *